United States Patent [19]

Joseph et al.

[11] 4,258,034
[45] Mar. 24, 1981

[54] LACTOBIONIC ACID POLY(H-SULFATE) AND SALTS THEREOF USEFUL AS COMPLEMENT INHIBITORS

[75] Inventors: Joseph P. Joseph, Cliffside Park, N.J.; Seymour Bernstein, New City, N.Y.

[73] Assignee: American Cyanamid Company, Stamford, Conn.

[21] Appl. No.: 91,214

[22] Filed: Nov. 5, 1979

[51] Int. Cl.[3] .................... A61K 31/70; C07H 11/00
[52] U.S. Cl. .................................... 424/180; 536/4; 536/118; 536/122
[58] Field of Search ............... 424/180; 536/118, 122, 536/4

[56] References Cited

U.S. PATENT DOCUMENTS

| | | | |
|---|---|---|---|
| 3,070,595 | 12/1962 | Petracek et al. | 536/118 |
| 3,075,965 | 1/1963 | Touey et al. | 536/118 |
| 3,200,110 | 8/1965 | Gollin et al. | 536/118 |
| 4,021,545 | 5/1977 | Nair et al. | 536/118 |
| 4,066,829 | 1/1978 | Nair et al. | 536/118 |

Primary Examiner—Johnnie R. Brown
Attorney, Agent, or Firm—Norton S. Johnson

[57] ABSTRACT

Lactobionic acid poly(H-sulfate) and salts thereof, useful as complement inhibitors.

14 Claims, No Drawings

LACTOBIONIC ACID POLY(H-SULFATE) AND SALTS THEREOF USEFUL AS COMPLEMENT INHIBITORS

BACKGROUND OF THE INVENTION

The present invention resides in the concept of lactobionic acid poly(H-sulfate) and salts thereof, which are novel compounds, and their use as inhibitors of the complement system of warm-blooded animals.

Partial sulfation products of maltose, as well as lactose, sucrose, manninotriose and stachyose are known, J. Pharm. Soc. Japan, 87, 1052 (1967). Sulfuric esters of maltose oligosaccharides have been prepared and their anti-coagulant activity investigated, Chemistry and Industry, October 982 (1952).

U.S. Pat. Nos. 2,686,779 and 2,697,093 disclose a method of preparing the alkali metal sulfates of polysaccharides, such as, cellulose, starch, inulin and dextrin, and U.S. Pat. No. 3,271,388 discloses the preparation of the alkali metal and ammonium salts of amylopectin sulfates useful as anti-coagulants. British J. Pharmacol; 7, 370 (1952) discloses sulfuric acid esters of starch and Acta. Physiologica Scand., 8, 215 (1945); 9, 28 (1945); 9, 35 (1945) and 110, 211 (1946) disclose sulfuric acid esters of starch having anti-coagulant and platelet agglutination activity. A sulfated polyglucose is known to possess anti-coagulant activity, Lab. Invest., 13 (8), 865 (1964). Certain sulfated polysaccharides are disclosed as having anti-inflammatory action, e.g., dextrin sulfate, pentosan polysulfate and amylopectin sulfate, Biochemical Pharmacology, 18, 1285 (1969). The sulfated polysaccharide heparin is known to have anti-complement activity, J. Infect. Disease, 44, 250 (1929). Pentosan polysulfo ester and dextran sulfate are also said to possess anti-complementary action, Pharmacology, 9, 74–79 (1973); Z. Naturforsch, 266, 403 (1971); Path. Biol., 25 (1), 33–36 (1977), 25 (2). 105–108 (1977), 25 (3), 179–184 (1977); Chemical Abst., 52, 485 h (1958); Fed. Proc. 140, 157 (1955); and 75, 33179 s (1971). Phlorizin (a compound containing glucose) is known to possess anti-complement activity, Bio-chemical Pharmacology, 23, 3107 (1974).

U.S. Pat. No. 4,020,160 discloses cyclodextrin sulfate salts as complement inhibitors. U.S. Pat. No. 4,021,544 discloses sulfated oligosaccharides of the maltose series as complement inhibitors. U.S. Pat. No. 4,021,5454 discloses inulin poly(H-sulfate) and salts thereof useful as complement inhibitors.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are desigantated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–58; 64–66; J. Allergy Clin. Immunol., 53, 298–302 (1974); Cold Spring Harbor Conf. Cell Proliferation 2/Proteases Biol. Control/229–241 (1975); Ann. Review of Biochemistry, 44, 697 (1975); Complement in Clinical Medicine, Disease-a-Month, (1975); Complement, *Scope,* December 1975; Annals of Internal Medicine 84, 580–593 (1976); "Complement: Mechanisms and Functions," Prentice-Hall, Englewood Cliffs, N.J. (1976); Essays Med. Biochem., 2, 1–35 (1976); Hospital Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1–8, 1195, 1358–1364, 1482 (1977).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)-piperazines useful as complement inhibitors. Other chemical compounds having complement inhibiting activity are disclosed in, for example, The Journal of Immunology, 93, 629–640 (1964); Journal of Medicinal Chemistry, 12, 415–419; 902–905; 1049–1052; 1053–1056 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim. Biophys. Res. Comm., 67, 225–263 (1974); Ann. N.Y. Acad. Sci., 256, 441–450 (1975); Journal of Medicinal Chemistry, 19, 634–639, 1079 (1976); Journal of Immunology, 118, 466 (1977); Arch. Int. Pharmacodyn., 226, 281–285 (1977); Biochem. Pharmacol. 26, 325–329 (1977); Journal Pharm. Sci., 66, 1367–1377 (1977); Chem. Pharm. Bull., 25, 1202–1208 (1977); Biochim. Biophys. Acta 484, 417–422 (1977) and Journal Clin. Microbiology, 5, 278–284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Interm. Med., 84, 580–593 (1976); J. Allergy and Clin. Immunology, 60, 38–40 (1977).

It has also been reported that the drug pentosanpolysulfoester has an anticomplementary activity on human serum, both in vitro and in vivo, as judged by the reduction in total hemolytic complement activity; Pathologie Biologie, 25, 33–36, 25 (2), 105–108, 25 (3), 179–184 (1977).

SUMMARY OF THE INVENTION

This invention is concerned with certain salts of sulfated lactobionic acid which interact with the complement reaction sequence, thereby inhibiting complement activity in body fluids.

This invention is particularly concerned with the pharmaceutically acceptable salts of sulfated lactobionic acid having the following formula:

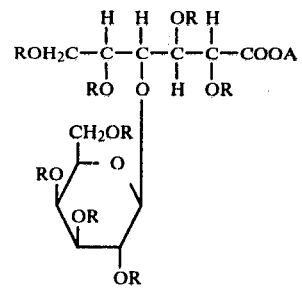

wherein R is $-SO_3A$; and A is a pharmaceutically acceptable salt cation.

Operable pharmaceutically acceptable salts encompassed within this invention include the salts of alkali metals, alkaline earth metals, ammonium and amines selected from triloweralkylamine ($C_1$–$C_6$), piperidine, pyrazine, alkanolamine ($C_1$–$C_6$) and cycloalkanolamine ($C_3$–$C_6$).

Representative compounds of the present invention include, for example, the following:

Lactobionic acid, octakis (H-sulfate), nonasodium salt.

Lactobionic acid, octakis (H-sulfate), nonatrimethylamine salt.

Other related sugar-bionic acids which may be used in the present invention, include, for example, the following: maltobionic acid, cellobionic acid and melibionic acid.

This invention is further concerned with a method of inhibiting the complement system in a body fluid, such as blood serum, which comprises subjecting said body fluid complement to the action of an effective complement inhibiting amount of a poly(H-sulfate) salt of a sugar bionic acid. Body fluid can include blood, plasma, serum, synovial fluid, cerebrospinal fluid or pathological accumulations of fluid such as pleural effusion, etc.

The method of use aspect of this invention is also concerned with a method of inhibiting the complement system in a warm-blooded animal, which comprises administering to said animal an effective complement inhibiting amount of a poly(H-sulfate) salt of a sugar bionic acid.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds of this invention may also be used in the therapeutic treatment of warm-blooded animals having non-immunologic diseases such as paroxysmal nocturnal hemoglobinuria, hereditary angioneurotic edema and inflammatory states induced by the action of bacterial or lysosomal enzymes on the appropriate complement components as, for example, inflammation following coronary occlusion. They may also be useful in the treatment of transplant rejection and as blood culture and transport mediums.

DESCRIPTION OF THE INVENTION

The sulfated sugar bionic acids encompassed within this invention may be prepared by application or adaptation of known methods, for example as described in Chemical Reviews, 62, 549–589 (1962) or in U.S. Pat. Nos. 2,686,779; 2,697,093; 2,923,704 and 3,271,388. For example, they may be prepared by dissolving or suspending the corresponding oligosaccharide in an organic solvent such as dimethylformamide at 20°–100° C. To this is added the salt forming substituent such as trimethylamine sulfur trioxide and the mixture is stirred and heated at 20°–100° C. for 8–28 hours. The addition of an organic solvent such as ethanol causes the precipitation of the poly(H-sulfate) salt which is collected by conventional methods and may be further purified by reprecipitation from organic solvents such as ethanol or ether, e.g., Chemical Reviews, ibid. The alkali or alkaline earth metal salts may be prepared by dissolving the above trialkylamine salts in water, adding aqueous alkali acetate and charcoal and filtering through diatomaceous earth. The filtrate is poured into ethanol causing precipitation of the poly(H-sulfate) alkali salt. This salt is again dissolved in water, alkali acetate is added and the salt is again precipitated from ethanol.

The compounds of the present invention may be administered internally, e.g., orally or parenterally, such as intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg. to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran, aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tables or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman anti-serum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, the results appear in Table I together with results of tests code 026, 035, 036 and Cap 50. Table I shows that the compounds of the invention possess highly significant in vitro and in vivo complement inhibiting activity in warm-blooded animals.

TABLE I

| Compound | Biological Activities | | | |
|---|---|---|---|---|
| | C1 026* Wells | C-Late 035* Wells | Shunt Inhibition 036* Wells | Cap 50* |
| Lactobionic acid, octakis (H-sulfate), nonatrimethylamine salt | 8** | 2 | 4 | 240 |
| Lactobionic acid, octakis (H-sulfate) nonasodium salt | 8 | 2 | 5 | 230 |

*Code designation for tests employed as referred herein.
**Activity in wells, a serial dilution assay. Higher well number indicates higher activity. The serial dilutions are two-fold.

DETAILED DESCRIPTION OF THE INVENTION

EXAMPLE 1

Lactobionic Acid, Octakis (H-Sulfate)

Nonatrimethylamine Salt

A solution of 4 g. of lactobionic acid in 50 ml. of dimethylformamide is treated with 16.2 g. of trimethylamine sulfur trioxide. The solution is heated at 60°-70° C. for 18 hours. The mixture is cooled and the resulting gum is collected by decantation. The gum is triturated sequentially with dimethylformamide, absolute ethanol and anhydrous ether and then dried in vacuo, giving the desired product.

EXAMPLE 2

Lactobionic Acid, Octakis (H-Sulfate)

Nonasodium Salt

A solution of one gram of lactobionic acid octakis (H-sulfate) trimethylamine salt in 5 ml. of distilled water is treated with 2.5 ml. of 30% aqueous sodium acetate. The mixture is poured with rapid mechanical stirring into 100 ml. of ethanol, producing a white flocculant precipitate. The solvents are removed by decantation. The residue is collected and washed with ethanol. The residue is purified by dissolving in water and reprecipitation from ethanol giving the desired product.

EXAMPLE 3

Preparation of Compressed Tablet

| Ingredient | mg/Tablet |
|---|---|
| Active Compound | 0.5-500 |
| Dibasic Calcium Phosphate N.F. | qs |
| Starch USP | 40 |
| Modified Starch | 10 |
| Magnesium Stearate USP | 1-5 |

EXAMPLE 4

Preparation of Compressed Tablet—Sustained Action

| Ingredient | mg/Tablet |
|---|---|
| Active Compound as Aluminum Lake*, Micronized | 0.5-500 (as acid) |
| Dibasic Calcium Phosphate N.F. | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 5

Preparation of Hard Shell Capsule

| Ingredient | mg/Capsule |
|---|---|
| Active Compound | 0.5-500 |
| Lactose, Spray Dried | qs |
| Magnesium Stearate | 1-10 |

EXAMPLE 6

Preparation of Oral Liquid (Syrup)

| Ingredient | % W/V |
|---|---|
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

Preparation of Oral Liquid (Elixir)

| Ingredient | % W/V |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

Preparation of Oral Suspension (Syrup)

| Ingredient | % W/V |
|---|---|
| Active Compound as Aluminum Lake, Micronized | 0.05-5 (acid equivalent) |
| Polysorbate 80 USP | 0.1 |
| Magnesium Aluminum Silicate, colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 9

Preparation of Injectable Solution

| Ingredient | % W/V |
|---|---|
| Active Compound | 0.05-5 |
| Benzyl Alcohol N.F. | 0.9 |
| Water for Injection | 100.0 |

EXAMPLE 10

Preparation of Injectable Oil

| Ingredient | % W/V |
|---|---|
| Active Compound | 0.05-5 |
| Benzyl Alcohol | 1.5 |
| Sesame Oil qs ad | 100.0 |

EXAMPLE 11

Preparation of Intra-Articular Product

| Ingredient | Amount |
|---|---|
| Active Compound | 2-20 mg. |
| NaCl (physiological saline) | 0.9% |
| Benzyl Alcohol | 0.9% |
| Sodium Carboxymethylcellulose | 1.5% |
| pH adjusted to 5.0-7.5 | |
| Water for Injection qs ad | 100% |

Example 12

Preparation of Injectable Depo Suspension

| Ingredient | % W/V |
|---|---|
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 13

Preparation of Dental Paste

| Ingredient | % W/V |
|---|---|
| Active Compound | 0.05-5 |
| Zinc Oxide | 15 |
| Polyethylene Glycol 4000 USP | 50 |
| Distilled Water qs | 100 |

EXAMPLE 14

Preparation of Dental Ointment

| Ingredient | % W/V |
|---|---|
| Active Compound | 0.05-5 |
| Petrolatum, White USP qs | 100 |

EXAMPLE 15

Preparation of Dental Cream

| Ingredient | % W/V |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 16

Preparation of Topical Cream

| Ingredient | % W/V |
|---|---|
| Active Compound | 0.05-5 |
| Sodium Laurylsulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |

-continued

| Ingredient | % W/V |
|---|---|
| Purified Water qs | 100 |

EXAMPLE 17

Preparation of Topical Ointment

| Ingredient | % W/V |
|---|---|
| Active Compound | 0.05–5 |
| Cholesterol | 3 |
| Stearyl Alcohol | 3 |
| White Max | 8 |
| Petrolatum, White USP qs | 100 |

EXAMPLE 18

Preparation of Spray Lotion (non-Aerosol)

| Ingredient | % W/V |
|---|---|
| Active Compound | 0.05–5 |
| Isopropyl Myristate | 20 |
| Alcohol (Denatured) qs | 100 |

EXAMPLE 19

Preparation of Buccal Tablet

| Ingredient | g/Tablet |
|---|---|
| Active Ingredient | 0.00325 |
| 6x Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 20

Preparation of Lozenge

| Ingredient | g/Lozenge |
|---|---|
| Active Ingredient | 0.0140 |
| Kompact Sugar (Sucrest Co.) | 0.7138 |
| 6 X Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

We claim:

1. A compound of the formula:

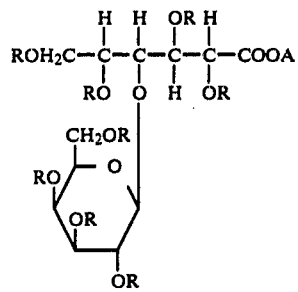

wherein R is —SO₃A; and A is a pharmaceutically acceptable salt cation.

2. The compound according to claim 1, lactobionic acid, octakis (H-sulfate) nonasodium salt.

3. The compound according to claim 1, lactobionic acid, octakis (H-sulfate) nonatrimethylamine salt.

4. A method of inhibiting the complement system in a body fluid which comprises subjecting said body fluid to the action of an effective complement inhibiting amount of a compound of the formula:

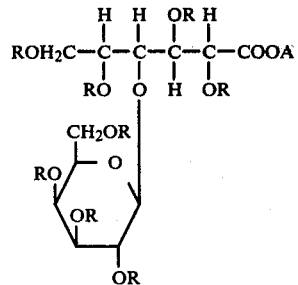

wherein R is —SO₃A; and A is a pharmaceutically acceptable salt cation.

5. A method according to claim 4, wherein the body fluid is blood serum.

6. A method according to claim 4, wherein the compound is lactobionic acid, octakis (H-sulfate) nonasodium salt.

7. A method according to claim 4, wherein the compound is lactobionic acid, octakis (H-sulfate) nonatrimethylamine salt.

8. A method of inhibiting the complement system in a warm-blooded animal which comprises administering to said animal an effective complement inhibiting amount of a compound of the formula:

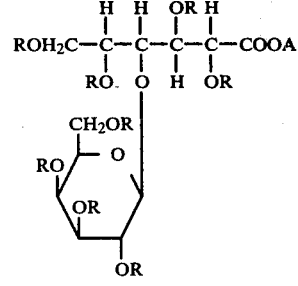

wherein R is —SO₃A; and A is a pharmaceutically acceptable salt cation.

9. A method according to claim 8, wherein the compound is administered internally.

10. A method according to claim 8, wherein the compound is administered topically.

11. A method according to claim 8, wherein the compound is administered periodontally in the oral cavity.

12. A method according to claim 9, wherein the compound is administered intra-articularly.

13. A method according to claim 8, wherein the compound is lactobionic acid, octakis (H-sulfate) nonasodium salt.

14. A method according to claim 8, wherein the compound is lactobionic acid, octakis (H-sulfate) nonatrimethylamine salt.

* * * * *